С005858781A

United States Patent [19]

Matyas et al.

[11] Patent Number: 5,858,781
[45] Date of Patent: Jan. 12, 1999

[54] METHOD OF TISSUE TRANSFER AND RETRIEVAL

[76] Inventors: John R. Matyas, 1606 21 Avenue N.W., Calgary Alberta, Canada, T2 M 1M1; Jerome B. Rattner, 35 Pt McKay Court, Calgary Alberta, Canada, T3B 5B7

[21] Appl. No.: 438,956

[22] Filed: May 11, 1995

Related U.S. Application Data

[63] Continuation-in-part of Ser. No. 242,290, May 13, 1994, abandoned.

[51] Int. Cl.$^6$ .................................................... C12N 5/06
[52] U.S. Cl. ........................................ 435/369; 435/284.1
[58] Field of Search .................... 435/240.2, 240.241, 435/284.1, 369

[56] References Cited

U.S. PATENT DOCUMENTS

| | | | |
|---|---|---|---|
| 2,591,927 | 4/1952 | Gladstone | 128/2 |
| 2,601,513 | 6/1952 | Gladstone | 128/2 |
| 4,853,324 | 8/1989 | Viles et al. | 435/2 |
| 5,153,132 | 10/1992 | Goodwin et al. | 435/240.24 |
| 5,316,754 | 5/1994 | Vlassara et al. | 424/2 |

FOREIGN PATENT DOCUMENTS

| | | |
|---|---|---|
| 2506017 | 11/1982 | France . |
| WO93/04193 | 4/1993 | WIPO . |

OTHER PUBLICATIONS

Mahnke, P.F., "Pathologica Polonica," vol. 28(3), pp. 401–407, 1977.
Carome, M.A. et al., "Am. J. of Physiology," vol. 264(6), pt. 2, pp. F923–29, Jun. 1993.
Bondestam, S. et al., "Scand. J. Urol. Nephrol.," vol. 26(3), pp. 265–267, 1992.
Wu, Z. et al., Chinese Journal of Ultrasonic Medicine, vol. 8(4), pp. 239–241, 1992.
Mostbeck, G.H. et al, "Optimal Needle Size for Renal Biopsy: In Vitro and In Vivo Evaluation", Radiology, vol. 173, 1989, pp. 819–822, Dec.
Benediktsson H. Et al, Enhanced Glomerular Retrieval in Renal Biopsies:, Clinical & Investigative Medicine (Annual Meeting of the Canadian Society for Clinical Investigation, Toronto, Sep. 1994), abstract. #537 p. B91.
Leet, N.G. et al, Rapid Method for Processing Entire Biopsy Pieces for Light and Electron Microscopy, Laboratory Practice, vol. 23, No. 2, Feb. 1974, pp. 59–60.
Taylor et al, "Tissue Printing as a Tool for Observing Immunological and Protein Profiles in Young and Mature Celery Petioles", 1993, Plant Physiol. 102:1027–1031.

*Primary Examiner*—Jean C. Witz
*Attorney, Agent, or Firm*—Brown, Pinnisi & Michaels, P.C.

[57] ABSTRACT

The Tissue Transfer method consists of transferring intact, organized cells from the surfaces of biological tissues or organs to a transfer substrate. A surface of the tissue or organ is selected, in most cases, a freshly cut surface. At least one layer of intact cells is transferred by adhesion of the cells to a transfer substrate, which is a membrane, film, plate or liquid layer bound to a solid structure. The substrate is brought into contact with the selected surface and removed. A layer of cells is removed by the adhesion of the cells to the substrate and the cells retain the organization of the organ or tissue. Method and apparatus for retrieving glomeruli dislodged from renal biopsy cores during the biopsy procedure and immobilizing the glomeruli on a membrane substrate. The morphological quality of these glomeruli is such that they can be used for diagnostic evaluation.

3 Claims, 11 Drawing Sheets

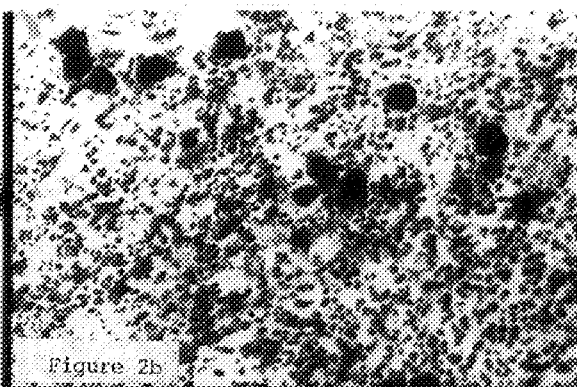
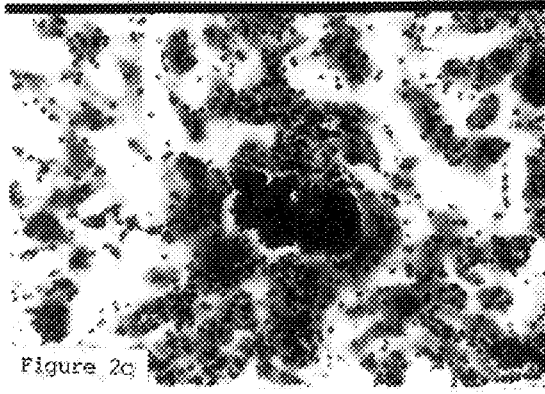
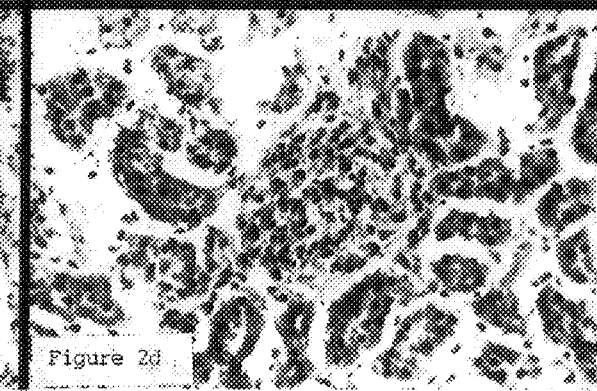

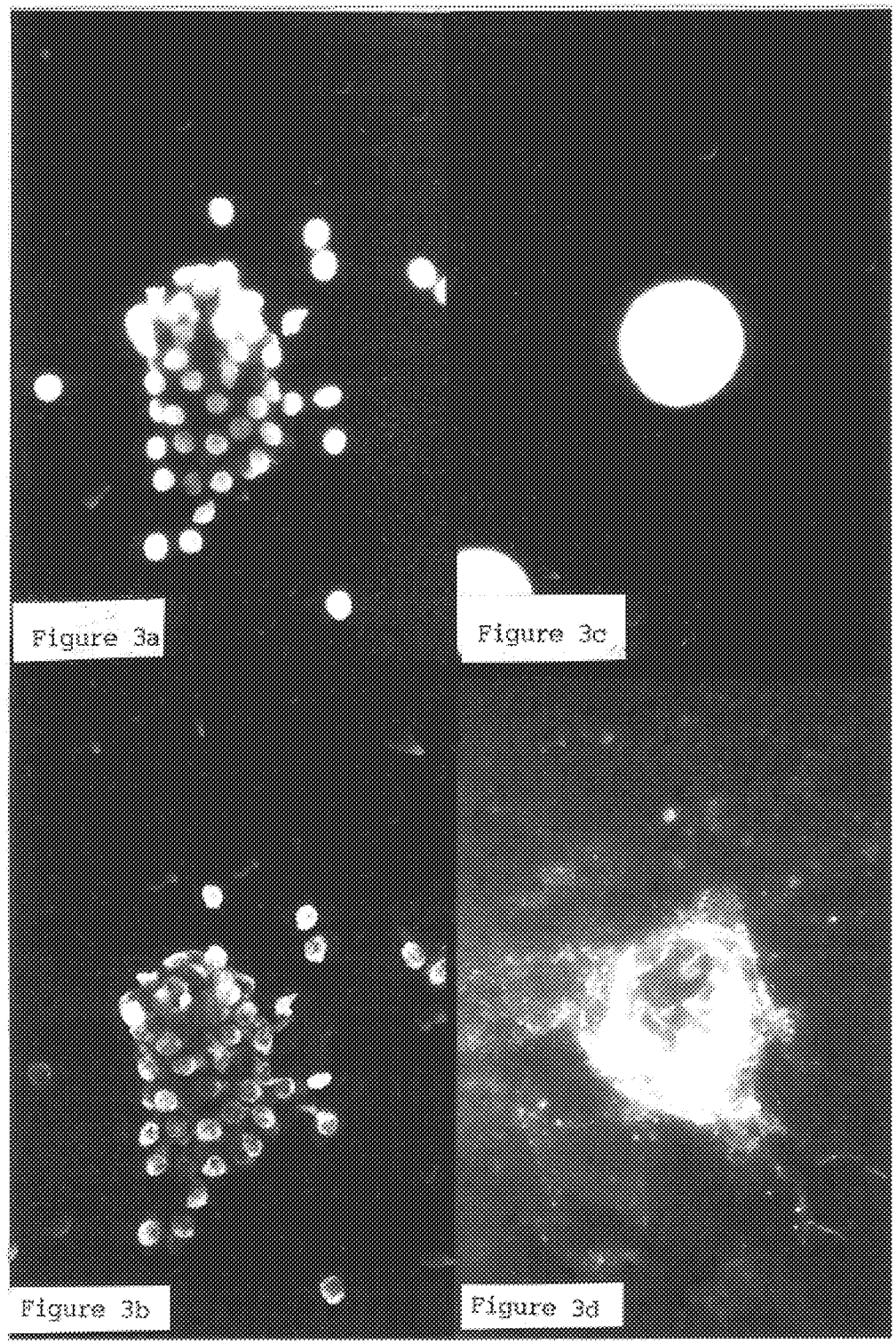

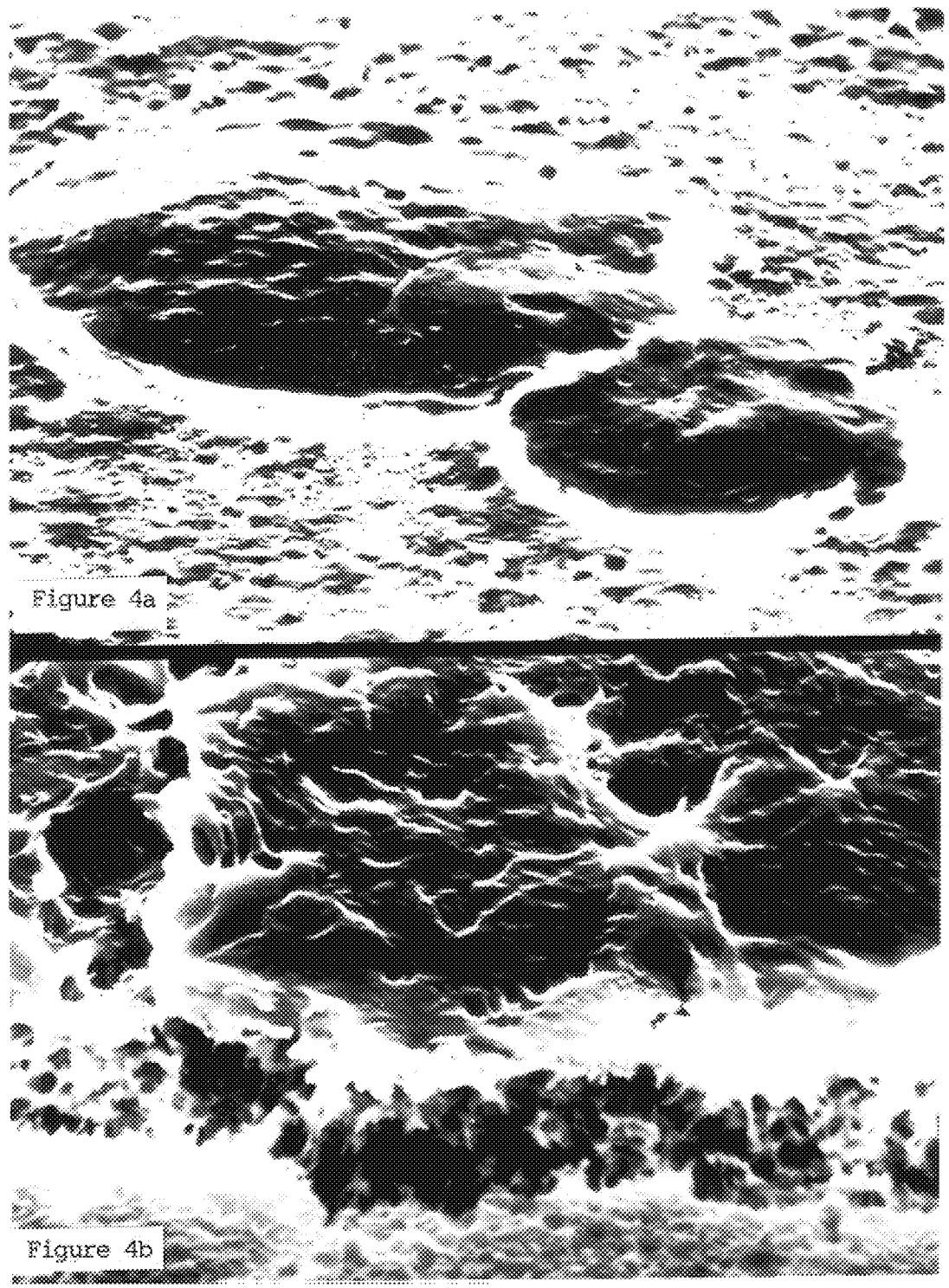

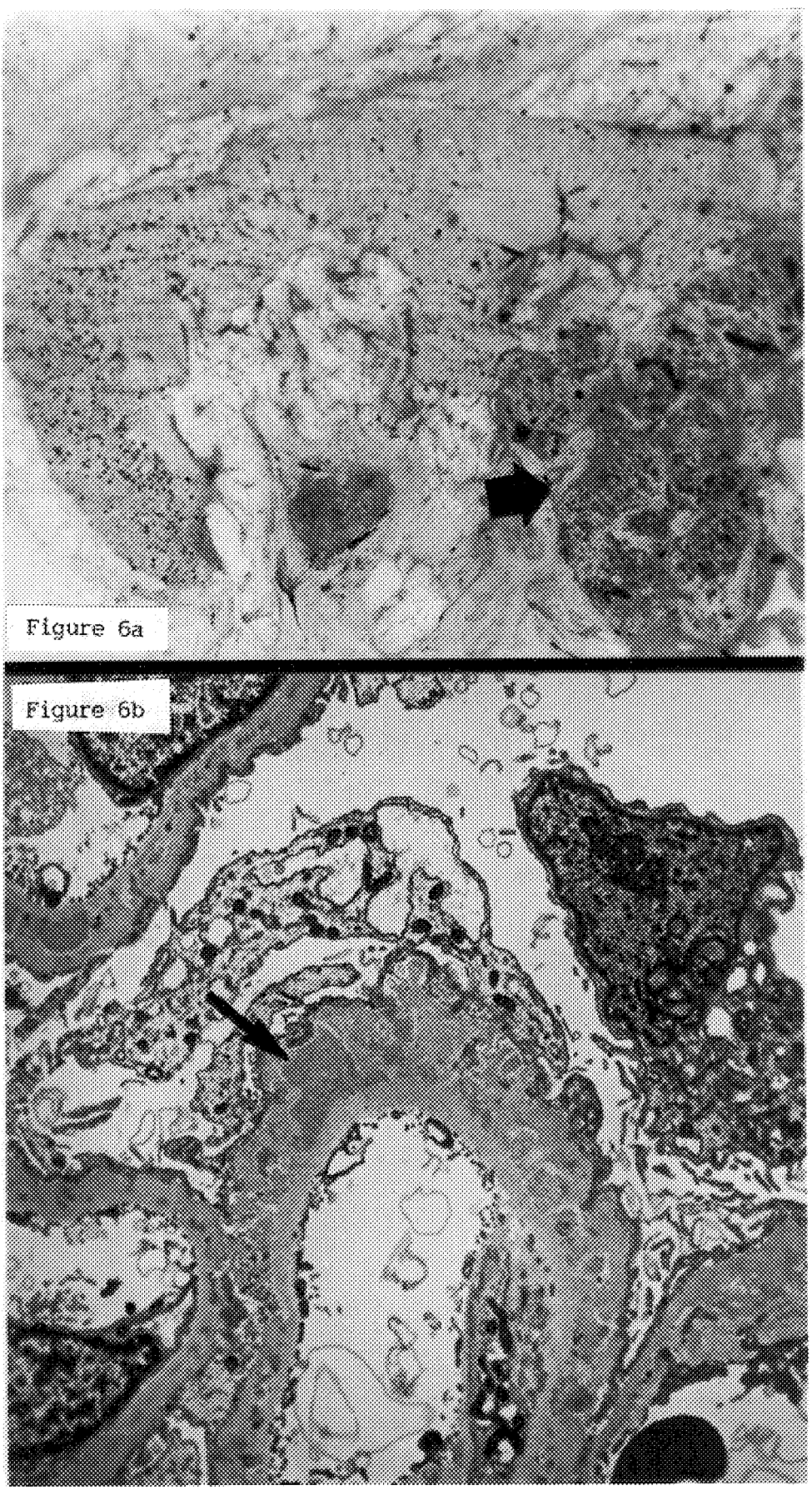

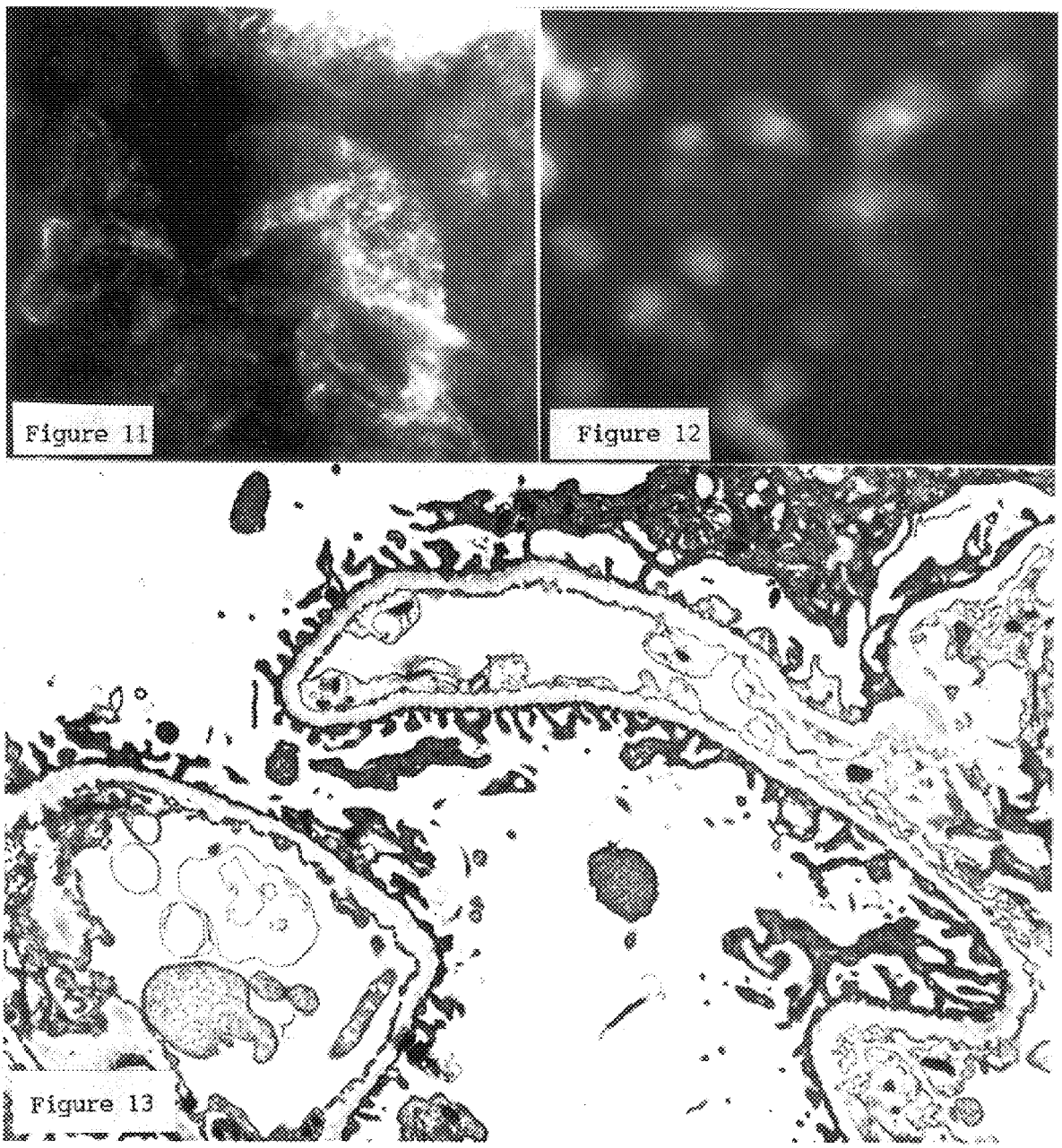

METHOD OF TISSUE TRANSFER AND RETRIEVAL

CROSS REFERENCE TO RELATED APPLICATIONS

This is a continuation-in-part application of application Ser. No. 08/242,290, filed May 13, 1994 entitled "METHOD OF TISSUE TRANSFER," now abandoned.

FIELD OF THE INVENTION

The invention pertains to the field of histology. More particularly, the invention pertains to the transfer of a sheet of cells from tissue or an organ to a membrane such that the cells retain tissue or organ architecture and organization and a method of retrieving tissue during a renal biopsy.

BACKGROUND OF THE INVENTION

Medical researchers and clinical physicians often isolate and examine tissue, individual cells, and macromolecules to gain a greater understanding of their patient's needs. Macromolecules come in four basic types: proteins (structural molecules, enzymes, etc.), carbohydrates (sugars that are often involved in cell surface recognition), lipids (fats including those that make up cell membranes), and nucleic acids (DNA and RNA). Cells are made up of all of these macromolecules and a good deal of water and small ions (sodium, potassium, chloride, etc.) The isolation and purification of specific macromolecules from biological tissues is the traditional realm of biochemistry, though this treatment of nucleic acids is now considered the realm of molecular biology.

The localization of specific macromolecules in tissue sections can be achieved by a variety of forms of histochemistry. Histology is the study of tissues, usually by cutting thin sections of tissue and looking at it under a microscope, the source of illumination may be visible light (traditional light microscopy), ultraviolet light (fluorescent microscopy), or electrons (electron microscopy). If a chemical reagent is used to identify a specific substance the method is simply termed histochemistry, if a reaction involves enzymatic catalysis, the term is enzyme histochemistry. When specific antibodies are used to identify a particular antigen (or epitope) in a tissue section, the terms used are immunohistochemistry, immunocytochemistry, or immunolocalization. When specific complementary sequences of nucleic acids are used to hybridize with specific cellular nucleic acids in tissue sections, the term used is in situ hybridization histochemistry.

The macromolecules of animal tissues are typically extracted, isolated, and purified before being separated by gel electrophoresis. Once separated, these macromolecules are generally transferred and immobilized on a membrane before being probed with specific antibodies or nucleic acids in the powerful and popular techniques of Northern, Southern, and Western hybridization.

In contrast to conventional blotting, in which macromolecules are transferred to a membrane along with their relative electrophoretic positions, "tissue prints" are believed to transfer molecules (from cell juices) along with their relative tissue locations. Some components of the "cell juice" are transferred to membranes during the tissue printing of botanical tissues, however, there is no evidence yet that whole cells or groups of cells are transferred in this process.

The technique of transferring macromolecules (including proteins and nucleic acids) directly from intact tissues to nitrocellulose or other blotting membranes has been called "tissue printing" (Varner, 1992). This technique has recently gained popularity in the field of plant science in large part because of the work of Cassab and Varner (1987). Botanical tissues are particularly well-suited or tissue printing because of their characteristic structural rigidity and symmetrical tissue architecture. It is, however, possible to make tissue prints of animal tissues as well.

One step further than a tissue print is isolating individual intact cells on nitrocellulose. In *Cell blotting: Techniques for staining and microscopical examination of cells blotted on nitrocellulose paper* (Anal. Biochem. 157:331–342, 1986), Seshi taught that individual isolated cells—both normal and neoplastic cells—can be immobilized onto nitrocellulose membrane with retained cytological detail. Seshi fails, however, to realize that the cells need not be digested and isolated. All the architectural information is lost by digesting and suspending his cells. This paper discusses the use of immunological agents to detect specific molecules (in this case the Leu-4 antigen on lymphocytes and chromogranin). This study also employs specific cell adhesion molecules, in this case fibronectin, to enhance the binding of cells, in this case BHK cells, to fibronectin-treated nitrocellulose membrane during a 60 minute incubation.

In *Ion channel expression by white matter glia: The type-i astrocyte* (Barres BA, Koroshetz, Chun LLY, Corey P., Neuron 5:527–544, 1990.), the authors describe what they call, "a new 'tissue print' dissociation procedure" to isolate individual cells from brain so that they could perform electrophysiology studies on them. These authors state that they wanted to use tissue printing to, "exploit this adhesion [between tissues and membranes] for cell isolation" and that they developed "an new 'tissue print' technique that produces dissociated cells . . . " (Barres et al., page 27). In some cases, brain tissue was partially digested before tissue printing onto nitrocellulose membrane; in other cases Vibrotome sections (50–100 micrometers thick) of brain tissue was printed onto nitrocellulose paper. These authors did recognize that live cells could be transferred to nitrocellulose substrata, but did not foresee the utility of the technique as a method of preserving the architectural arrangement of cells from large tissues, indeed, they developed the method for cell isolation so that they could perform electrical experiments on isolated cells with intact cell processes. In the discussion these authors state that, "The tissue print protocol is a simple variant of standard dissociation protocols." and that " . . . rather than shearing the tissue apart by passage through a syringe needle or pipette, a 'touch prep' [a technique used in clinical pathology] is prepared by gently touching the tissue to a sticky, nontoxic surface." They go on to say, "Unlike previous methods, this tissue print procedure allows isolation of viable cells still bearing processes for further study. Here we have used tissue prints for electrophysiological recording; however, we have also used the procedure for other purposes, including isolation of cells for culture, scanning electron microscopy, and immunohistochemistry." Notably, they do not mention transmission electron microscopy nor do they discuss anything about pathological tissues.

In *Simultaneous recording of [Ca2+]i increases in isolated olfactory receptor neurons retaining their original spatial relationship in intact tissue* (Hirono J, Sato T, Tonoike M, Takebayashi M., J. Neurosci. Meth. 42:185–194, 1992) the authors teach that small slices of olfactory epithelium (i.e., smelling nerves) can be dissected and digested before "unrolling" a piece of tissue onto a glass substrate coated with the lectin Concanavalin A as an adhesive. These authors state that the "relative local arrangement between the cells" is preserved. It should be pointed out that this technique involves very small pieces of tissue with the purpose of preparing the cells for tissue culture and from the pictures shown, the tissue and organ architecture is poorly preserved.

Currently, there is no technique for transferring layers of animal tissue that retain the tissue and organ architecture and are viable when transferred.

The renal biopsy is an essential diagnostic tool for a wide variety of renal disorders. The procedure has, until recently, involved the use of 12–18 gauge needle devices, such as the vim-Silverman biopsy needle, which are associated with a small but significant risk of serious hemorrhage complications. Large gauge needles have fallen out of favor with the recent development and popularization of various biopsy gun devices, which are typically equipped with smaller (16–18 gauge) needles. These devices reduce patient morbidity, but also yield smaller biopsy specimens. As the assessment of glomerular pathology remains one of the most important objectives of the renal biopsy procedure, it is essential that each biopsy contain an adequate number of glomeruli. Whereas the mean yield from larger biopsy cores is routinely 25–75 glomeruli per core, the yield from smaller cores is often less than 10. At the lower end of this range the number of glomeruli is frequently inadequate to make a proper diagnosis.

It is possible to calculate the number of glomeruli within a cylindrical biopsy of known dimensions now that an unbiased estimate of the numerical density of glomeruli in normal autopsied human kidney has been reported. Such estimates are substantially higher than the number of glomeruli typically found in clinical renal biopsy specimens. This analysis, together with the clinical observation that spheroidal voids (the shape and size of a glomerulus) are observed on the biopsy surface, suggests that glomeruli become separated from the biopsy core during or after the biopsy procedure. Therefore, a need exists for improving the yield of the biopsy procedure.

SUMMARY OF THE INVENTION

It is the primary object of the present invention to teach a method of transferring intact, organized cells from the surfaces of biological tissues or organs to a substrate such hat the cells retain the organization of the organ or tissue.

It is an additional object of the present invention to teach a method of retrieving issue during a renal biopsy and specifically glomeruli.

The present invention teaches that not only are certain molecules transferred to the membranes, but indeed whole cells or sheets of cells are transferred from animal tissues to these membranes. Hence the technique is more appropriately called "Tissue Transfers" or "Tissue Stripping." Animal cells are adsorbed, stripped away, and transferred from cut surfaces of fresh animal tissues to membrane substrates with high fidelity with respect to tissue and organ architecture and histomorphology.

The localization of specific macromolecules in histological sections of plant and animal tissues is usually done by conventional immunohistochemistry and in situ hybridization histochemistry. Whereas these techniques offer high spatial resolution, they are labor-intensive and require considerable proficiency. Although generally of lower spatial resolution (Cassab and Varner, 1987), tissue prints from plants yield satisfactory resolution for many purposes while offering substantial advantages in speed and simplicity during tissue preparation and hybridization. Hence, the development of the Tissue Transfer Process for animal tissues is especially useful for screening large numbers of tissues or for studying tissues of large size for the presence and localization of specific cells and macromolecules.

The method consists of transferring intact, organized cells and groups of cells from the surfaces of biological tissues or organs to a substrate. A surface of the tissue or organ is selected, in most cases, a freshly cut surface. At least one layer of intact cells is transferred by adhesion of the cells to a transfer substrate, which is a membrane, film, plate or liquid emulsion layer bound to a solid structure. The substrate is brought into contact with the selected surface and removed. A layer of cells is removed by the adhesion of the cells to the substrate and the cells retain the organization of the organ or tissue.

The Tissue Transfer Technique is a simple and efficient new method that offers several advantages over conventional techniques (of histology, cell culture, immunoblotting, and Northern blotting). It does not, however, wholly displace them. The Tissue Transfer Technique is an alternative to conventional techniques in certain circumstances where speed, large samples, access to cell surfaces, or archival storage are required at a substantial savings in cost.

The first advantage is that morphological and chemical information can be obtained and analyzed considerably faster than with conventional histological processing. Typically, the Tissue Transfer Technique can be done in less than a minute and fixation, histochemical staining, and examination can be complete in many cases in as little as 5–10 minutes. In addition, multiple samples can be obtained from the same freshly cut tissue surface thereby supplying additional and control Tissue Transfers for investigation. Due to the high fidelity of Tissue Transfer architecture, the transfers are potentially useful as a substrate for the rapid screening of tissue morphology, chemistry, enzymology, immunology, and molecular biology.

A second advantage of the Tissue Transfer process is that the surface of very large tissues (e.g. whole kidneys, large solid tumors), which otherwise would have to be cut in small pieces, can be transferred intact. This facilitates the analysis of global variation in morphology or chemistry across very large tissue samples.

A third advantage of the Tissue Transfer Technique is that more of the cell surface is exposed for study since the cells are transferred intact and their surfaces are exposed without sectioning. There is a calculated increase in cell surface area available to study of at least 50% for spheroidal cells, 150% for cuboidal cells, and even greater increases for more irregularly shaped cells. This advantage has important implications in the study and characterization of neoplastic cells, for example, where cell surface molecules are believed to play an important role in intercellular signaling and metastasis (Travis, 1993). The thinness of the tissue layer that is transferred also confers a distinct advantage for ultrastructural studies because fixation is rapid and complete.

A fourth advantage is that the Tissue Transfer Technique is that certain opaque membranes (nitrocellulose but not nylon) can be clarified by immersion in solvents of similar refractive index (e.g., xylene) and can then be mounted onto a glass slide. This feature is quite remarkable because at first glance the resulting Tissue Transfers bear a similarity to histological sections. This makes possible a direct qualitative comparison between traditional histological sections (frozen and paraffin sections) and clarified tissue prints. This development has aided immensely our understanding of what and how cellular material is transferred during the Tissue Transfer Technique and has given comfort to the pathologists who feel more at home looking at traditionally prepared tissues. The pathologists now recognize that Tissue Transfers offer information that is qualitatively different and otherwise unavailable in conventional preparations.

A fifth practical advantage of the Tissue Transfer Technique is that the transferred sheets of cells can be cultured on sterilized membranes. Since the cultured Tissue Transfers maintain the architectural features of the intact organ they offer potential as "organ monolayer cultures" that can be used to study cell and tissue physiology as well as for screening pharmacological agents and assessing tissue toxicology.

A sixth practical advantage is that the Tissue Transfer Technique is easily mastered and can be carried out by laboratory personnel trained in standard cytological techniques. Furthermore, the technique can be carried out at very low cost making it accessible technology for a variety of large and small scale applications.

The present invention also includes using the knowledge gained from implementing the Tissue Transfer Technique to improve the yield during a renal biopsy. The present inventors have discovered that a numeric discrepancy exists between the expected and actual number of glomeruli found in renal biopsy specimen. This discrepancy can be accounted for, at least in part, by the loss of glomeruli during the biopsy procedure. Glomeruli can be lost at several different stages of the biopsy procedure. Most of these "lost" glomeruli accumulate in the fluid used to dislodge the core from the biopsy gun. The glomeruli in this fluid can be collected and preserved by a simple and direct method.

The method comprises filtering the "lost" glomeruli from the fluid used to dislodge the core from the biopsy gun. The filter is preferably a nitrocellulose filter. The filter with the glomeruli can then be used for pathological study.

The present invention includes an apparatus for filtering the "lost" glomeruli from the fluid used to dislodge the core from the biopsy gun. The filtering apparatus comprises a chamber for holding the fluid, a means for securing a filter and a suction device for drawing the fluid through the filter.

This method and device dramatically improve the yield of renal biopsies. The glomeruli retrieved can be used along with the biopsy core for pathological study or archiving. The recovered tissue on the nitrocellulose membrane can be used in the same manners as a layer of cells obtained by the Tissue Transfer Technique above.

BRIEF DESCRIPTION OF THE DRAWING

FIGS. 2a–d show organ, tissue and cellular morphology of a rabbit kidney using various Tissue Transfer preparations.

FIGS. 3a–d show immunofluorescent studies of a rabbit kidney using various Tissue Transfer preparations.

FIGS. 4a and 4b show pictures of various Tissue Transfer preparations of a rabbit kidney using a scanning electron microscope.

FIGS. 6a and 6b show pathological morphology studies of a human kidney using various Tissue Transfer preparation.

FIG. 11 shows a picture of an indirect immunofluorescence pattern of a membrane-immobilized glomerulus reacted with fluorescein isothiocyanate (FITC)-conjugated coctail of anti-IgM and anti-IgA antibodies.

FIG. 12 shows the same image as FIG. 11 filtered to reveal DNA with DAPI (4',6 diamino 2 phenylindole) counter stain.

FIG. 13 shows an electron micrograph of a membrane-immobilized glomerulus.

DESCRIPTION OF THE PREFERRED EMBODIMENT

Figure 1A:
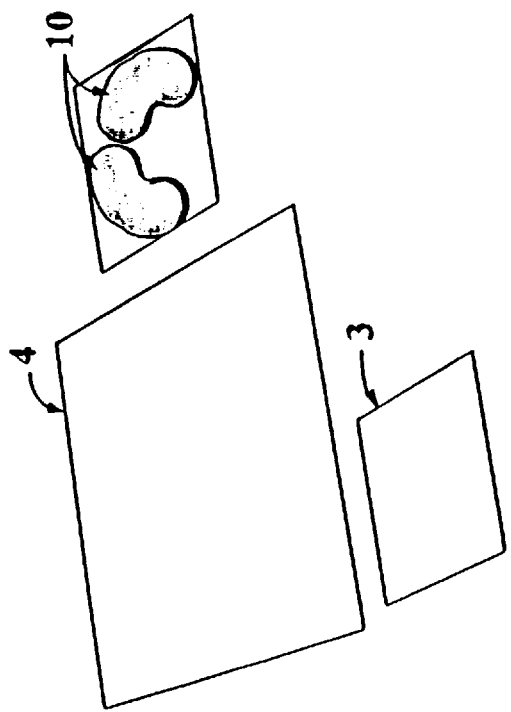
FIGS. 1a–d illustrate the steps involved with making a Tissue Transfer from a freshly cut piece of tissue to a membrane.

In the scientific literature, there have been a limited number of studies describing what has been called "tissue printing" where proteins and nucleic acids can be shown to be transferred from the cut surfaces of cells onto membranes (Reid et al., 1992). Tissue printing has been used primarily with plant tissues because their cell walls are structurally rigid facilitating printing and the symmetrical tissue architecture of plants facilitates morphological analysis. Tissue printing of plant tissues is qualitatively different than Tissue Transfers of animal tissues, since whole cells are not transferred to the substrates. The novelty of the Tissue Transfer Technique is that it allows the transfer of cells, and sheets of cells, while preserving native tissue architecture.

There are also reports that suspensions of isolated cells can be immobilized and examined cytologically on some substrates. These protocols, however, are not useful in applications where tissue and organ histomorphology are a prerequisite. The Tissue Transfer Technique differs from those in which cell suspensions are applied to filters, or cellular material is absorbed to a medium, in that the Tissue Transfer Technique provides the transfer of a tissue layer which retains high fidelity with respect to tissue and organ architecture and histomorphology. In addition, intercellular associations are maintained in the section plane.

The utility of the Tissue Transfer Technique is that cells, groups of cells, and their macromolecular constituents can be immobilized on a substrate while maintaining tissue architecture. Once immobilized, cell, tissue or organ morphology, chemistry, lectin affinity, enzyme activity, immunoreactivity, and nucleic acid composition can all be explored as a function of organ architecture and tissue location. For example, specific molecules can be detected and mapped across an organ: alkaline phosphatase enzyme activity can be localized in prostates and growth plate chondrocytes, antibody antigen complexes can be localized in the glomeruli of the renal cortex, estrogen receptor mRNA can be localized in breast carcinomas, lectins can be used to identify vascular cells in a tumor of unknown origin, antimitotic spindle antibodies can be used in identify the number and location of dividing cells in tumors, etc. Thus, the Tissue Transfer Technique has numerous potential applications in surgical pathology including the study of morphology, identification of specific cell surface receptors, diagnosis of mitotic rate/malignant grade, the identification of tumor margins, adhesion molecule density, and tumor archiving. Furthermore, using the appropriate sterilized substrates, the Tissue Transfer Technique can be carried out on surgically excised tissue as well as tissue margins remaining within the patient.

Another important advantage is that the Tissue Transfer Process exposes more cell surface area to the investigator for examination (approximately 50% more in the case of spherical cells; at least 150% more in the case of cuboidal cells). This is particularly important since it is widely believed that cell surface molecules play a central role in malignancy and the Tissue Transfer Process gives you "more to work with".

The Tissue Transfer Technique has considerable utility in industrial scientific settings and in basic science research when screening large number of tissues (e.g., to see the effect of different drugs on liver metabolism) or a large number of animals (e.g., to see the expression of a particular reporter gene in transgenic animals). In addition, the Tissue Transfer Technique is almost unique in its ability to examine the continuous distribution of a particular cell or macromolecule in very large organs (e.g., whole livers, whole brains, large solid tumors) which would otherwise have to be cut into smaller pieces for processing by traditional techniques.

It is possible to maintain Tissue Transfers in culture. Since the Tissue Transfers maintain sheets of cells with their native cell-to-cell arrangement, Tissue Transfers offer unique advantages over established (i.e. immortalized) cell lines or cells that have been digested from intact tissues and grown in culture (i.e., primary cell cultures).

FIGS. 1a–d illustrate the steps involved with making a Tissue Transfer from a freshly cut piece of tissue to a membrane. FIG. 1a shows a rabbit kidney 1 being cut with a razor blade 2. New, clean single-sided razor blades work well, however, other sharp blades, including autopsy knives, may be used. For small tissue samples razor blades and scalpels work well; for larger tissues, particularly those that arrive at the pathology bench, an autopsy knife (really just an elongated scalpel blade) works even better.

Figure 1B:
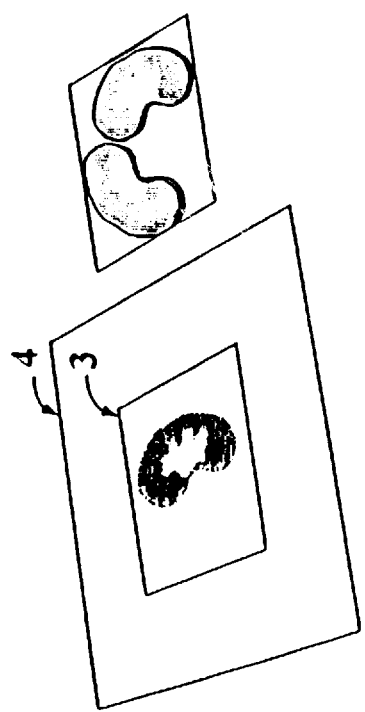

FIG. 1a shows a whole rabbit kidney 1 about to be cut in half with a razor blade 2. A large square of blotting paper 3 (e.g. Whatmann 3 MM chr™ chromatography paper) is placed on the benchtop; a smaller square of membrane 4, transfer substrate, (e.g. Pall BioDyne™ membrane) is cut and positioned in the middle of the blotting membrane 3. FIG. 1b shows the rabbit kidney 1 cut in half exposing the newly cut kidney surface 10. Gloves are usually worn, particularly if RNA is to be preserved.

Figure 1C:
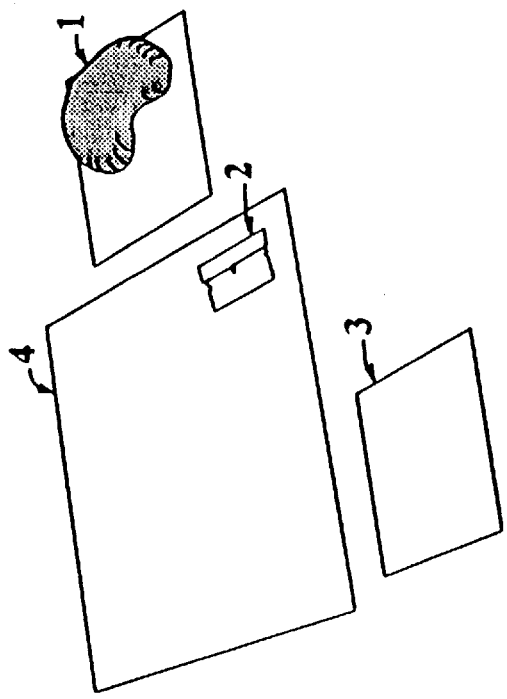

FIG. 1c shows one half of kidney 1 placed cut-surface 10 down onto the membrane 4. Depending on the size of the organ, gentle pressure may be applied. After about 30 seconds, a time that can vary, the kidney 1 is carefully lifted from the membrane 4 or the kidney-membrane complex is inverted and the membrane 4 is peeled from the surface 10 of the kidney.

Figure 1D:
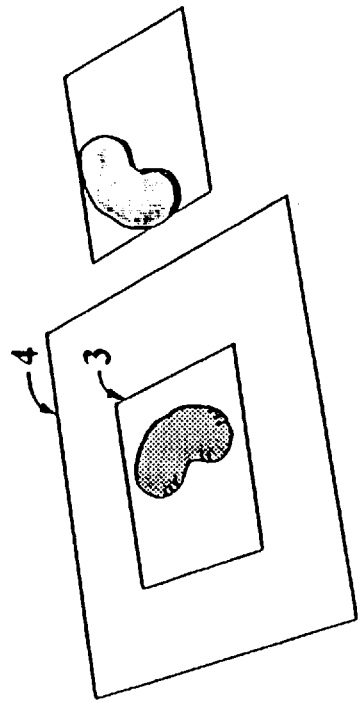

FIG. 1d shows that a slight impression, some tissue fluid and some blood allows the kidney 1 to be faintly visible on the membrane 4. The same cut surface can be printed again (though the efficiency of transfer diminishes with each successive transfer) onto a fresh piece of membrane. The transfer can be fixed; e.g. neutral-buffered formalin (NBF).

The Tissue Transfer Technology has been used to transfer cells and cell layers from a variety of normal tissues (including kidney, liver, heart, muscle, ligament, lymph nodes, spleen, brain and developing bone) to a variety of different substrates. We have established that excellent cellular, tissue and organ morphology is maintained by using the Tissue Transfer Technique. As shown in the FIGS. 2–6, cells and their components can be faithfully transferred to the substrate with the preservation of the tissue architecture in the section plane. Architecture, ultrastructure, and epitopes are all preserved during the Tissue Transfer Technique.

FIGS. 2a–d show organ, tissue and cellular morphology of a rabbit kidney using various Tissue Transfer preparations. In FIG. 2a a whole rabbit kidney has been divided in half and transferred onto a nylon membrane (ICN BioTrans™) by the Tissue Transfer Technique. The resulting Tissue Transfer has been fixed with formaldehyde, stained with toluidine blue O, rinsed in ethanol, and photographed with reflected light. The overall characteristic shape of the kidney can be discerned as can the characteristic internal architecture: the outer (darker) region is the renal cortex and the inner (lighter) region is the renal medulla. The dark dots visible in the renal cortex are renal glomeruli, which are the site in the kidney where urine is filtered from the blood. The magnification in this photograph is approximately 1.8×.

FIG. 2b shows a higher magnification of kidney cortex transferred to nitrocellulose membrane (Schleicher & Schuell S&S NC™ BA85, 0.45 micrometer pore size), fixed in 3% paraformaldehyde, and stained with hematoxylin and eosin. The membrane has been clarified in xylene, the Tissue Transfer has been mounted under a coverglass on a glass microscope slide, and photographed by transmitted light. A number of glomeruli are visible as dark dots scattered among renal tubules. The approximate magnification is 16×.

FIG. 2c shows a higher magnification of a preparation similar to that in FIG. 2b. A single renal glomerulus is shown nested among kidney tubules. The approximate magnification is 150×.

For comparison with conventional histology, FIG. 2d shows a 5 micrometerthick frozen tissue section of the same kidney used to make the Tissue Transfer in FIG. 2c, stained with hematoxylin and eosin, and photographed with transmitted light. A single renal glomerulus is shown nested among kidney tubules. The approximate magnification is 300×.

The selection of a transfer substrate is important. To date the best success has been with nitrocellulose or nylon paper. The relative efficiency with which sheets of cells are transferred by the Tissue Transfer Technique depends on the substrate: different tissues work better with different substrates. Substrates can be chosen from a variety of transfer membranes (e.g., nitrocellulose, nylon, PVDF, etc.), films, plates, and emulsion layers.

FIGS. 3a–d show immunofluorescent studies of a rabbit kidney using various Tissue Transfer preparations. FIG. 3a shows a Tissue Transfer of rabbit kidney onto nylon membrane (Pall BioDyne™—0.45 micrometer pore size) fixed in methanol. A fluorescent histochemical counter stain for DNA (DAPI=4',6-diamino-2-phenylindole) shows the location of renal tubule cells. The approximate magnification is 625×.

FIG. 3b shows the same preparation as in FIG. 3a incubated with human anti-DNA primary antibody. Goat anti-human antibody conjugated with fluorescein was used as a secondary antibody to detect the human anti-DNA antibody, which reacts with rabbit DNA. This illustrates that nuclear epitopes are preserved during Tissue Transfers. The approximate magnification is 625×.

FIG. 3c shows a high magnification of rabbit kidney Tissue Transfer. DNA fluorescence is due to DAPI counter stain. The approximate magnification is 1500×. FIG. 3d shows the same preparation as in FIG. 3c incubated with human anti-tubulin primary antibody. Fluorescein-conjugated goat anti-human secondary antibody was used to detect the human anti-tubulin antibody. Tubulin, a polymeric cytoskeletal protein is seen in a network throughout the cytoplasm of the cell. This illustrates that cytoplasmic epitopes are preserved by the Tissue Transfer Technique. The approximate magnification is 1500×.

FIGS. 4a and 4b show pictures of various Tissue Transfer preparations of a rabbit kidney using a scanning electron microscope. FIG. 4a shows a Tissue Transfer of rabbit kidney onto nylon membrane (BioDyne™), fixed in acetone, sputter-coated with gold-palladium, and examined by scanning electron microscopy. The two disc-shaped objects are renal glomeruli. This preparation shows the retention of tissue architecture and the three-dimensional features of glomeruli in Tissue Transfers. The approximate magnification is 1300×. FIG. 4b shows a higher magnification of the same preparation shown in (a). This photomicrograph was taken at the border between the membrane (below) and the larger renal glomerulus (above). The approximate magnification is 2600×.

Figures 5A, 5B:
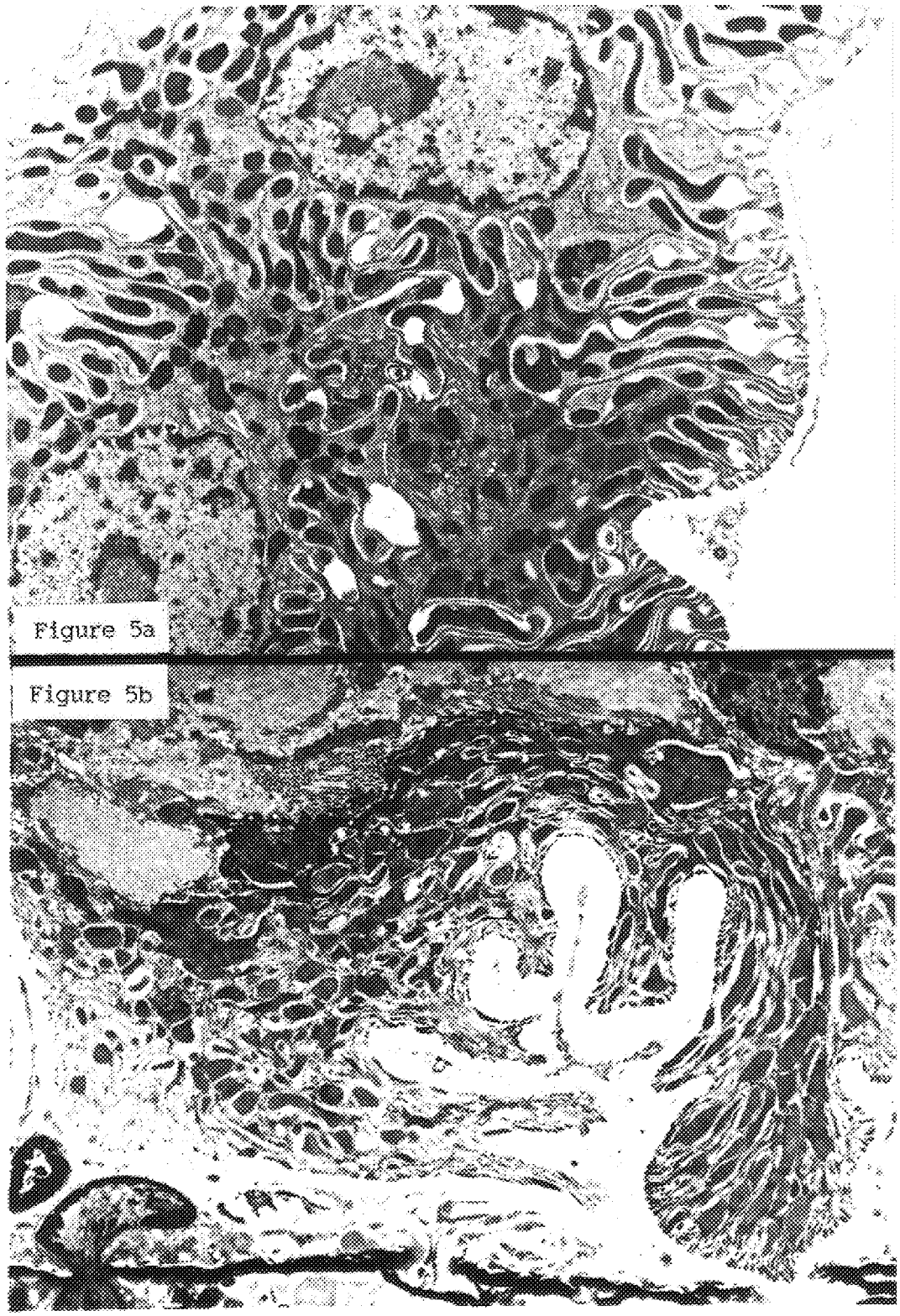
FIGS. 5a and 5b show pictures of various Tissue Transfer preparations of a rabbit renal tubule using a transmission electron microscope.

FIGS. 5a and 5b show pictures of various Tissue Transfer preparations of a rabbit renal tubule using a transmission electron microscope. FIG. 5a shows and electron micrograph of Tissue Transfer of rabbit renal tubule fixed in glutaraldehyde, post-fixed in osmium tetroxide, and stained with lead citrate and uranyl acetate. Two nuclei can be seen as well as numerous mitochondria. The extensive infolding of the cytoplasmic membrane is characteristic of these cells. The basement membrane of the tubule is on the right; membrane off to the left. This micrograph illustrates the excellent morphological preservation of all the cellular organelles including membranes that is possible in Tissue Transfers. The approximate magnification is 10,000×.

FIG. 5b shows an electron micrograph of Tissue Transfer of rabbit renal tubule. The surface of the nylon membrane is visible as a dark line along the bottom. As in FIG. 5a the ultrastructural features of the cells and organelles are well preserved. An interesting feature of this micrograph is the preservation of a nucleus that appears to have been partially sucked down through a pore in the membrane (lower left). This type of morphological feature suggests that the mechanism whereby cells and tissues are adsorbed onto the surface of the membrane involves capillary action. (Alternatively, it is possible that even gentle pressure "sieves" organelles.) The approximate magnification is 12,500×.

FIGS. 6a and 6b show pathological morphology studies of a human kidney using various Tissue Transfer preparations. FIG. 6a shows a very low magnification (approximately 1.25×) of a Tissue Transfer on nitrocellulose of a human kidney. The characteristic outline of the kidney is visible in this Tissue Transfer which has been stained with hematoxylin and eosin and mounted on a glass slide. The glomeruli are clearly visible as dark dots in the renal cortex and a mass of malignant cells (a renal cell carcinoma) is clearly visible to the right of the arrow. The margins of the tumor are clearly visible macroscopically as well as microscopically. This illustrates the utility of Tissue Transfers to identify tumor margins in large tissues.

FIG. 6b shows an electron micrograph of Tissue Transfer of a human renal glomerulus that has been retrieved from a renal biopsy. The definitive diagnosis of lupus nephritis was made on this Tissue Transfer; the arrow points out the characteristic electron-dense immune complex deposits in the glomerular basement membrane. The preservation of ultrastructure is excellent. The approximate magnification is 7,500×.

While the primary utility of the Tissue Transfer Technique is the transfer of large pieces of tissue while retaining tissue architecture, the technique of isolating cells on a transfer membrane can also be used as a method for harvesting material routinely lost during biopsy sampling. It is possible to use the isolation procedure to harvest large and small fragments of biopsy material that are very difficult to collect by conventional procedures. This recovered material has been studied by light and electron microscopy. This material retains its morphological and chemical characteristics and can be used in diagnostic studies along with material harvested by conventional means. The transfer of biopsy material to a transfer membrane may help save glomeruli that are lost during renal biopsy. This may make it possible to minimize patient morbidity (fewer or extra biopsies) and to maximize the material available to pathological diagnosis hence increasing the accuracy of the diagnosis. The Tissue Transfer Technique can also be used to study renal and breast tumors.

The Tissue Transfer Technique has proven the advantages of immobilizing cells or groups of cells on porous membranes. The present inventors have discovered that the yield of renal biopsies can be improved greatly by filtering the fluid used to dislodge the biopsy core from the biopsy gun through a porous membrane. The "lost" glomeruli are then immobilized on the membrane and can be used for histological or pathological study.

The volume and surface area of a cylindrical biopsy can be calculated from the dimensions of commonly used biopsy needles, which typically have internal diameters ranging from 2.0 mm (14 gauge) to 1.6 mm (16 gauge) to 1.2 mm (18 gauge) and chamber lengths ranging from 10 to 15 mm (Hopper et al.). Since normal glomeruli are spheroidal particles approximately 150 micrometers in diameters glomeruli whose centers lie outside but near the surface of the biopsy cylinder may be contained within the core sample. Indeed, a normal glomerulus would likely be "hit and seen" even if 140 micrometers of its diameter lies outside the biopsy cylinder. Thus, the "effective total volume" of a biopsy, with respect to the number of glomeruli observed, includes the volume of an annular cylinder surrounding the biopsy core. For this analysis, the effective volume is calculated as:

$$\pi^*(\text{cylinder radius}+140\ \mu M)^{2*}\text{cylinder height}.$$

The product of effective volume and numerical density of glomeruli equals the total number of glomeruli visible within an ideal intact biopsy core. Similarly the number of glomeruli cut by the biopsy needle, i.e., those on the surface of the biopsy specimen, can be estimated. Since glomeruli with their centroids within 140 micrometers of the surface of the biopsy core would actually be cut and exposed by the needle, the "effective surface volume" is a 280-micrometer-thick "pipe" formed by the "outer" and "inner" annular cylinders. The product of this volume and the numerical density of glomeruli equals the number of glomeruli exposed on the surface of an ideal intact biopsy core. It is these "exposed" glomeruli that are most at risk of becoming dislodged from the biopsy core during processing.

Figure 7:
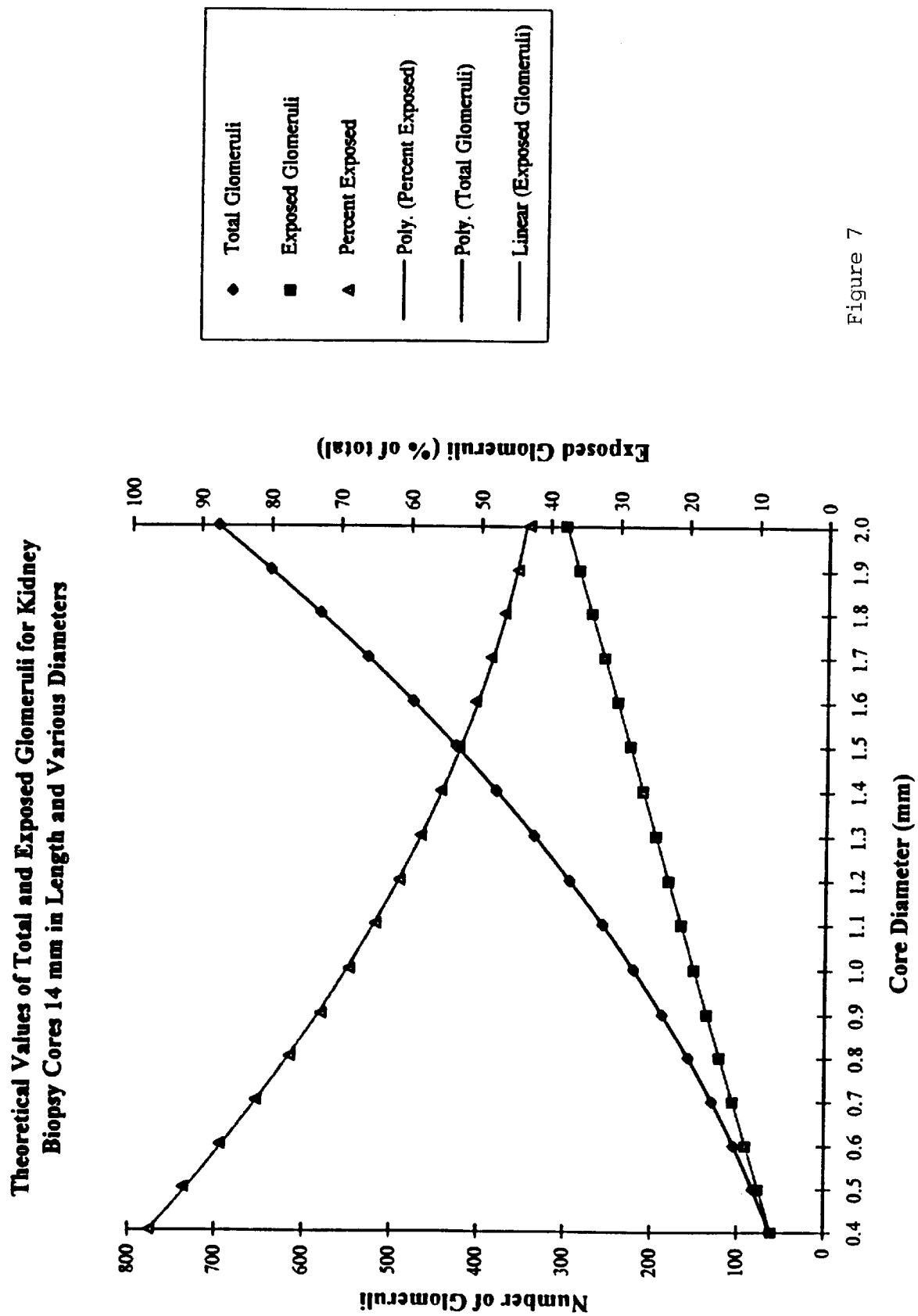
FIG. 7 shows a plot of the number of glomeruli that would theoretically be associated with the effective total volume and the effective surface volume of biopsy cores 14 mm in length and various diameters.

The numerical density of glomeruli from normal kidneys at autopsy is approximately 12.27 glomeruli per cubic millimeter. Based on this value, the total number of glomeruli in the effective volume is plotted for kidney biopsies 14 mm in length and various diameters and is shown in FIG. 7. The number of exposed glomeruli is also plotted in FIG. 7, as is the percentage of the total number of glomeruli that are exposed. The number of glomeruli obtained using 18 gauge biopsy needles is often less than 10 . Thus, the foregoing theoretical analysis suggested that a significant population of glomeruli are unaccounted for during the standard biopsy procedure--regardless of biopsy needle diameter. To determine the fate of these "lost" glomeruli a preliminary experimental animal study was performed to try and retrieve any lost glomeruli and to determine if this loss occurred at any particular stage of the biopsy procedure.

Three female 12-month-old, New Zealand white rabbits (Reimans Fur Ranches, St. Agatha, Ont., Canada) were euthanized by an overdose of intravenous barbiturate. These animals were cared for under the supervision of a veterinarian and were a part of an orthopedic study that did not alter kidney structure or physiology. The kidneys were removed, placed on the laboratory bench, and three biopsy cores of the kidney cortex were taken with an 18 gauge biopsy gun with chamber dimensions 1.2 mm diameter by 15 mm length. Rabbit kidney biopsies were handled similarly to clinical biopsies (see below). Briefly, to remove them from the needle, biopsy cores were gently agitated in 100 ml of sterile phosphate-buffered 0.9% saline in a stainless steel dish. The biopsies were picked up with a sterile 18 gauge hypodermic needle, transferred to a glass microscope slide covered with several drops of saline, and examined with a dissecting microscope. The length and caliper width of the biopsy were measured with an eyepiece graticule: all cores were intact cylinders measuring approximately 1.0 mm in diameter and 12.0 mm in length. Biopsies were fixed in neutral-buffered formalin in a scintillation vial.

To ascertain if any glomeruli became dislodged during removal of the core from the biopsy needle, the saline in the stainless steel dish was filtered by suction through a nylon transfer membrane (BioDyne, 0.45 micrometer pore size, Pall, Inc., Glen Cove, N.Y., USA). The filter was held on a 25 mm support (Nalge)and suction was applied with a 50 ml syringe. To see if any glomeruli were dislodged from the core during manipulation on the glass slide, a small piece of membrane was used to "blot" the saline left on the surface of the slide. This method of immobilizing small fresh pieces of tissue on membrane substrates has been described above as the Tissue Transfer Technique. The biopsy needle, stainless steel dish, hypodermic needle, glass slide, scintillation vial, and nylon membranes were all stained with 1% aqueous toluidine blue 0 and examined carefully using a dissecting microscope. Rabbit glomeruli were identified by their characteristic morphological appearance. Toluidine blue-stained membranes, needles, and equipment revealed glomeruli or fragments of glomeruli were recovered at every stage of the biopsy procedure. Only glomeruli, or large fragments of glomeruli that were clearly identifiable as glomeruli, were enumerated. The various phases of the biopsy procedure when glomeruli are lost, i.e. dislodged, from the biopsy core, is illustrated for one rabbit (a series of three biopsies) in Table 1.

TABLE 1

| Location | Number of Glomeruli |
| --- | --- |
| Biopsy Gun Needle | 1 |
| Hypodermic Needle | 1 |
| Glass Slide | 5 |
| Slide "Blot" Membrane | 35 |

TABLE 1-continued

| Location | Number of Glomeruli |
| --- | --- |
| Stainless Steel Dish | 50 |
| Filtered Saline Membrane | 35 |

This study showed that at least some lost glomeruli become dislodged from the biopsy core during each stage of the biopsy procedure, and that most of these dislodged glomeruli reside in the fluid used to remove the core from the biopsy gun. Thus, we sought to establish if substantial numbers of intact human glomeruli could be found in the saline used for clinical renal biopsies.

Figure 8A:
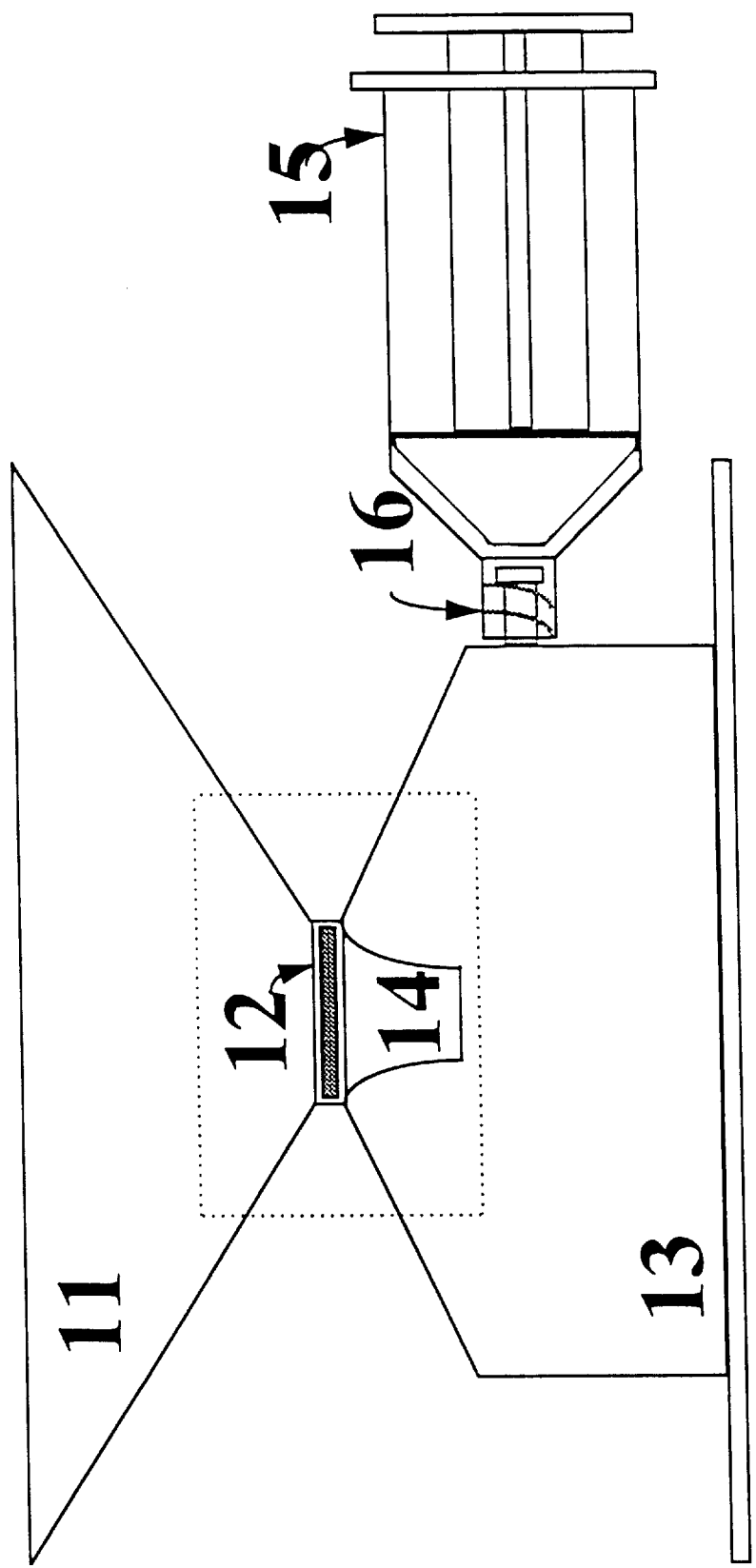
FIGS. 8a and 8b show the glomeruli retrieval device in an cross-sectional view and exploded view respectively.
Figure 8B:
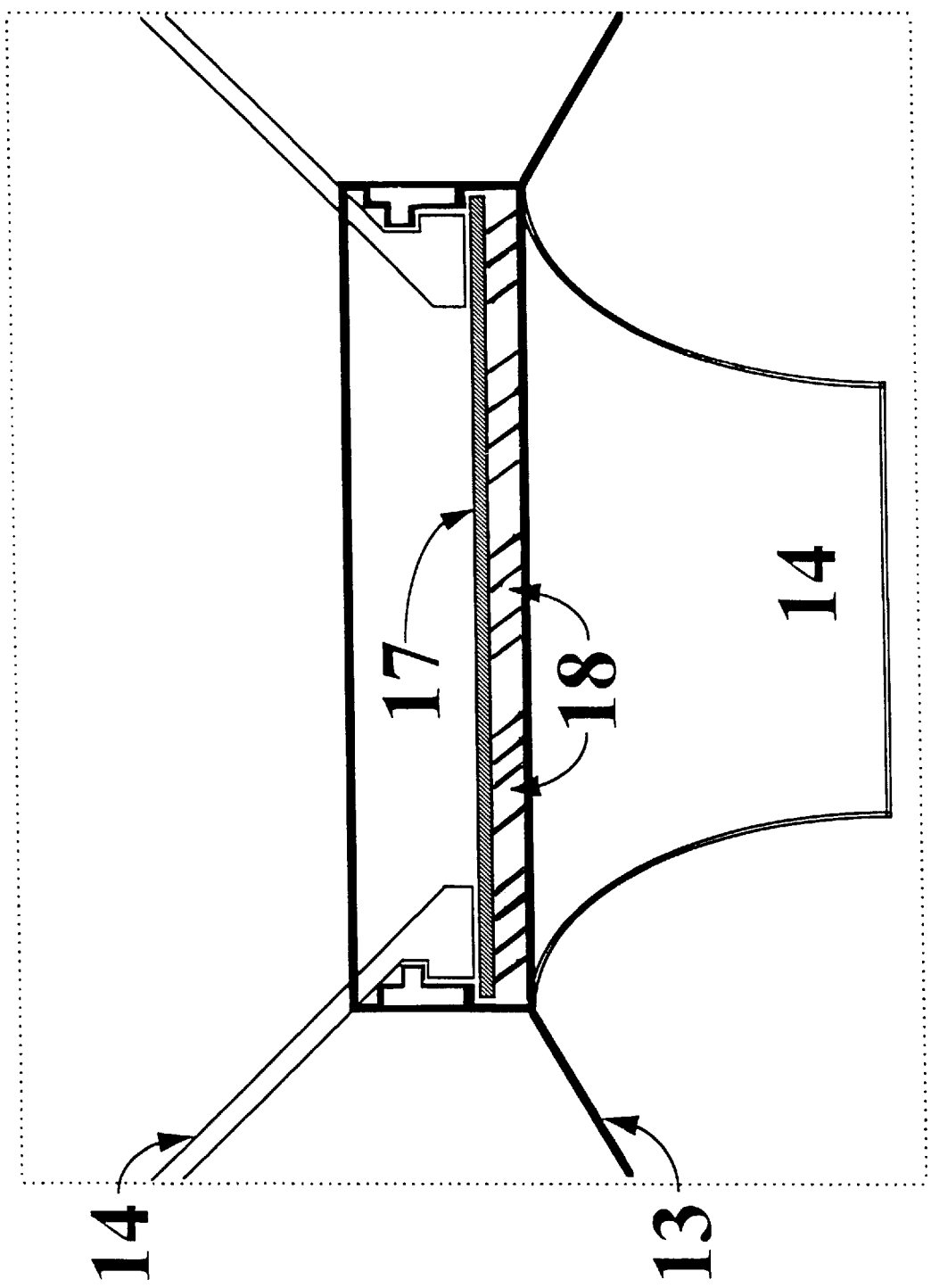

A glomeruli retrieval device was developed and is shown in FIGS. 8a and 8b. A funnel shaped reservoir 11 that snaps or screws into a filter support 12, in which a porous membrane substrate 17 is supported. The reservoir 11 holds the membrane 17 in place. The filter support 12 itself is supported by a base 13, which is a sealed container. Directly beneath the filter support 12 is a manifold 14 to direct the filtered fluid into the base 13. On the side of the base is a Leur-lok type fitting 16 to accomodate a standard syringe 15. The syringe 15 is used to withdraw air form the base 13 chamber such that a pressure differential is created across the membrane 17. The pressure differential draws the fluid in the reservoir 11 across the membrane 17.

FIG. 8b shows an exploded view of the filter support 12 and the membrane 17. The membrane 17 had a pore size of 0.20 to 0.45 micrometers One embodiment for securing the resevoir 11 to the filter support 12 is shown wherein the reservoir 11 is screwed or snapped into the filter support 12. The membrane 17 lies directly on an interupted plastic support 18 that gives firm support of the membrane while allowing a pressure differential to form across the membrane 17. As the syringe 15 is pulled the fluid is drawn across the membrane 17 and any glomeruli previously in the fluid are immobilized on the membrane 17.

Forty-five patients with various renal diseases underwent renal biopsy at the Foothills Hospital (Calgary, Alberta, Canada). Patients were placed in the lateral decubitus position, a local anesthetic was administered, and a kidney was visualized by ultrasonography. Through a small scalpel incision, the needle of an 18 gauge biopsy gun (Bard, Monopty 18 or ASAP 18 ) was guided by ultrasound to the surface of the kidney and "fired". This was repeated using the same gun until 2 or 3 biopsy cores were obtained.

Once removed from the patient, the biopsy gun was "reloaded" and the biopsy core was released by agitating the needle in 20 ml of 0.9% saline in a stainless steel tray. The core was then lifted from the metal tray with a 12 gauge syringe needle, placed on a microscope slide covered with approximately 0.5 ml of saline, and observed with a dissecting microscope. Cores judged suitable for histopathology were then transferred to containers containing appropriate fixatives and buffers for further processing (see below). Typically, one biopsy core was processed for histopathology, one for ultrastructural pathology, and one for immunopathology.

The biopsy core for histopathology was fixed in neutral phosphate-buffered 10% formalin, dehydrated in ethanol, and embedded in Historesin. Serial sections 2 micron-thick sections were cut, stained with a toludine blue-silver methenamine. The number of glomeruli in each biopsy was counted from these serial sections. The biopsy core for immunopathology was held in buffer, embedded in O.C.T. compound, and quick frozen in liquid nitrogen-cooled isopentane. Five micrometer-thick cryosections were cut. The biopsy core for electron microscopy was cut into three or more small cylinders before fixation in glutaraldehyde dehydrate, embedded, sectioned, and examined.

Based on our preliminary animal study, we chose to enumerate "lost" glomeruli by collecting and immobilizing them on membranes as described above. Membrane-. immobilized glomeruli were collected from: (1) filtering the saline solution in the metal tray, (2) blotting the walls of the metal tray after the saline had been poured out, and (3) blotting the microscope slide. We learned that it was possible to maximize the recovery of glomeruli that may have settled to the bottom of the metal dish, by gently agitating the dish just before pouring the saline solution into a sterile 50 ml polypropylene tube. This fluid was held on ice until transported back to the laboratory where it was filtered through a piece of BioDyne membrane as described above. All of the membranes used to immobilize glomeruli were fixed immediately after blotting or filtering.

Membrane-bound glomeruli were processed for electron microscopy by fixing in 3% glutaraldehyde in Millonig's phosphate-buffered saline pH 7.5 and postfixing in phosphate-buffered 1% $OsO_4$. The membranes were then washed in distilled water and prestained with 2% aqueous uranyl acetate. The membranes were dehydrated in a graded series of ethanol. Ethanol was replaced with 2-hydroxypropyl methacrylate, and the membranes were embedded in Epon 812 in the bottom of a plastic petri dish. Following polymerization at 60° C., the Epon slab was removed from the dish and selected areas containing glomeruli (which were distinctly visible as black globes, which could be easily distinguished from other tissue fragments under the dissecting microscope) were cut and mounted on the tip of a blank Epon block. Thin sections were cut on a LKB ultramicrotome, collected on copper grids, and stained with 2% uranyl acetate and 1% lead citrate. Samples were examined in a Hitachi H7000 microscope at 75 kV. The ultrastructural quality of membrane-immobilized glomeruli was satisfactory for diagnostic purposes in all cases. The fine structure of the podocytes, mesangial cells, and the basement membrane was clearly visible and well preserved.

Figures 9, 10:
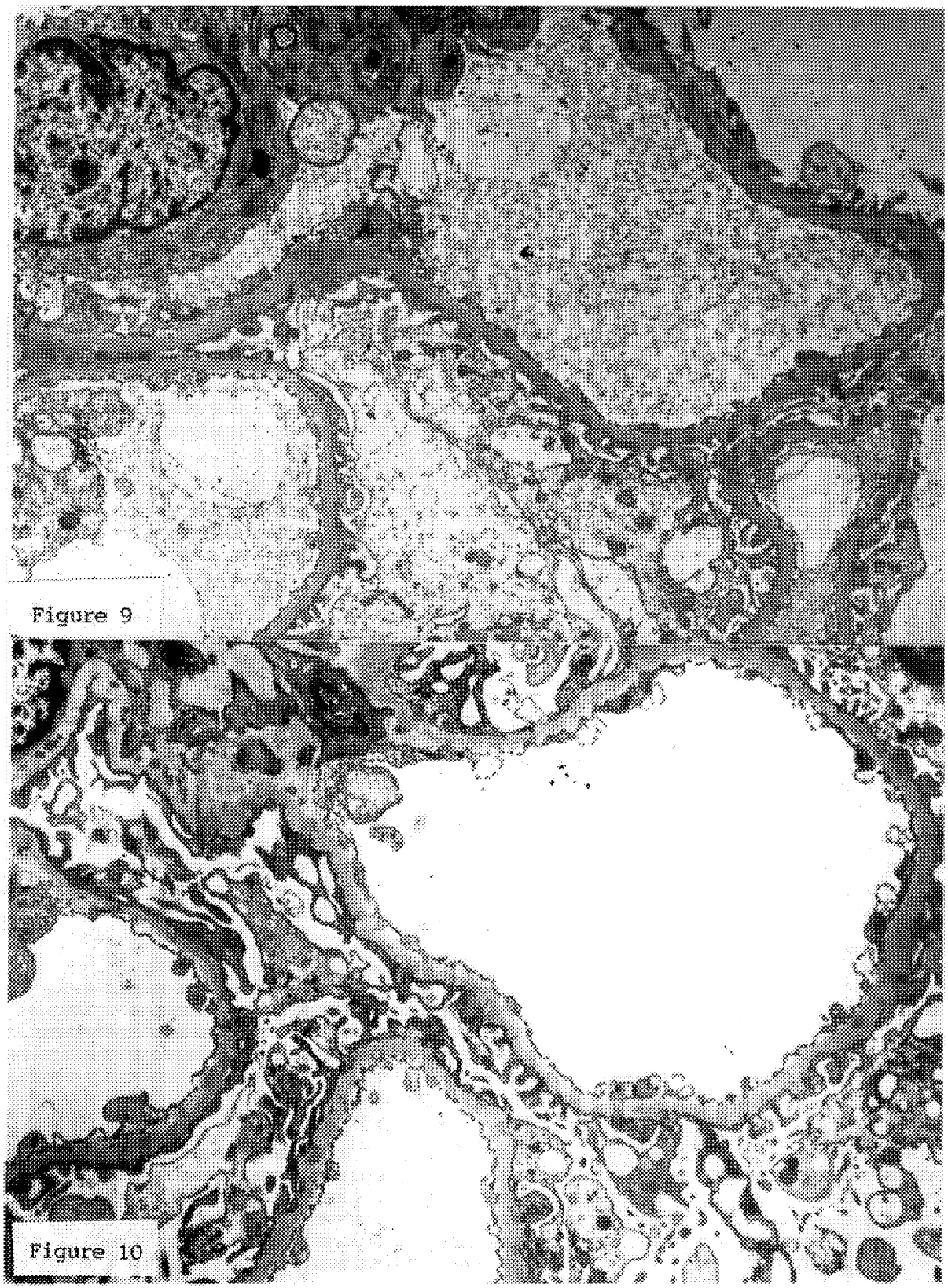
FIG. 9 shows a picture of electron micrograph of glomeruli from the biopsy core.
FIG. 10 shows a picture of electron micrograph of glomeruli on the membrane substrate retrieved from the biopsy procedure used to obtain the core show in FIG. 9.

During the initial phases of this clinical study we discovered that it was possible to reduce the total time needed to process the retrieval membrane for electron microscopy to just one day without compromising ultrastructure. Retrieved glomeruli were compared with glomeruli from the core sample taken from the same individual (FIGS. 9 and 10). FIG. 9 shows a picture of electron micrograph of glomeruli from the biopsy core. FIG. 10 shows a picture of electron micrograph of glomeruli on the membrane substrate.

These samples displayed comparable morphology and were evaluated independently to arrive at the same diagnosis. In many instances, the glomeruli on the membranes had superior morphology, in terms of the fine structure to those of the biopsy core. Twenty-five consecutive patients were studied to determine the relative proportion of the total number of glomeruli that could be recovered from the saline. The number of glomeruli per biopsy core ranged from 7 to 39; the number of glomeruli immobilized on membrane ranged from 0 to 22. These and other data from this series patients is catalogued in Table 2. By retrieving and immobilizing dislodged glomeruli on membrane it was possible to increase the average yield of glomeruli 26.1% with a standard deviation of 15.2%, with a range of 0–55%.

TABLE 2

| Patient # | Sex | Diagnosis | Biopsy Gun | # of Biopsies | # Glomeruli per biopsy |
|---|---|---|---|---|---|
| 1 | M | Acute Tubular Necrosis | ASAP | 1 | 9 |
| 2 | F | Acute Rejection | ASAP | 2 | 11 |
| 3 | M | Chronic Glomerulonephritis | ASAP | 2 | 11 |
| 4 | M | IgA Nephropathy | ASAP | 2 | 11 |
| 5 | F | IgA Nephropathy | ASAP | 2 | 17 |
| 6 | M | Thin Membrane Disease | ASAP | 2 | 11 |
| 7 | M | Nephrosclerosis | Monopty | 2 | 8 |
| 8 | M | Nephrosclerosis | Monopty | 2 | 7 |
| 9 | F | Lupus Nephritis | Monopty | 2 | 11 |
| 10 | F | Lupus Nephritis | Monopty | 2 | 18 |
| 11 | M | IgA Nephropathy | ASAP | 3 | 18 |
| 12 | M | IgA Nephropathy | ASAP | 3 | 25 |
| 13 | M | Minimal Change Disease | ASAP | 3 | 22 |
| 14 | M | IgA Nephropathy | ASAP | 3 | 22 |
| 15 | M | Membranous Glomerulonephritis | ASAP | 3 | 23 |
| 16 | M | Acute Rejection | Monopty | 3 | 22 |
| 17 | F | Focal Glomerulosclerosis | Monopty | 3 | 17 |
| 18 | M | Membranous Glomerulonephritis | Monopty | 3 | 33 |
| 19 | M | Amyloidosis | Monopty | 3 | 30 |
| 20 | M | Chronic Tubular Interstitial Nephritis | Monopty | 3 | 39 |
| 21 | F |  | Monopty | 3 | 17 |
| 22 | M | Crescentic Glomerulonephritis (Wegner's) | Monopty | 3 | 15 |
| 23 | F | Diabetic Nephropathy | Monopty | 3 | 12 |
| Max |  |  |  | 3.0 | 39.0 |
| Min |  |  |  | 1.0 | 7.0 |
| Mean |  |  |  | 2.5 | 17.8 |
| StDev |  |  |  | 0.6 | 8.3 |
| Median |  |  |  | 3.0 | 17.0 |

TABLE 2-continued

| Patient # | Saline | Tray | Slide | Recovered Glomeruli | Recovered Glomeruli per biopsy | Total Glomeruli | % of Total Glomeruli Recovered |
|---|---|---|---|---|---|---|---|
| 1 | 1 | 1 | 1 | 3 | 3.0 | 12 | 25.0 |
| 2 | 2 | 0 | 2 | 4 | 2.0 | 15 | 26.7 |
| 3 | 4 | 0 | 2 | 6 | 3.0 | 17 | 35.3 |
| 4 | 6 | 0 | 0 | 6 | 3.0 | 17 | 35.3 |
| 5 | 7 | 0 | 0 | 7 | 3.5 | 24 | 29.2 |
| 6 | 5 | 0 | 3 | 8 | 4.0 | 19 | 42.1 |
| 7 | 2 | 0 | 0 | 2 | 1.0 | 10 | 20.0 |
| 8 | 1 | 0 | 0 | 1 | 0.5 | 8 | 12.5 |
| 9 | 1 | 0 | 0 | 1 | 0.5 | 12 | 8.3 |
| 10 | 21 | 0 | 1 | 22 | 11.0 | 40 | 55.0 |
| 11 | 19 | 1 | 1 | 21 | 7.0 | 39 | 53.8 |
| 12 | 0 | 0 | 0 | 0 | 0.0 | 25 | 0.0 |
| 13 | 8 | 0 | 3 | 11 | 3.7 | 33 | 33.3 |
| 14 | 2 | 0 | 0 | 2 | 0.7 | 24 | 8.3 |
| 15 | 14 | 0 | 3 | 17 | 5.7 | 40 | 42.5 |
| 16 | 6 | 0 | 0 | 6 | 2.0 | 28 | 21.4 |
| 17 | 1 | 0 | 0 | 1 | 0.3 | 18 | 5.6 |
| 18 | 6 | 0 | 3 | 9 | 3.0 | 42 | 21.4 |
| 19 | 10 | 0 | 10 | 20 | 6.7 | 50 | 40.0 |
| 20 | 2 | 0 | 0 | 2 | 0.7 | 41 | 4.9 |
| 21 | 5 | 0 | 2 | 7 | 2.3 | 24 | 29.2 |
| 22 | 3 | 0 | 1 | 4 | 1.3 | 19 | 21.1 |
| 23 | 4 | 0 | 1 | 5 | 1.7 | 17 | 29.4 |
| Max | 21.0 | 1.0 | 10.0 | 22.0 | 11.0 | 50.0 | 55.0 |
| Min | 0.0 | 0.0 | 0.0 | 0.0 | 0.0 | 8.0 | 0.0 |
| Mean | 5.7 | 0.0 | 1.4 | 7.2 | 2.9 | 25.0 | 26.1 |
| Stdev | 5.6 | 0.3 | 2.2 | 6.7 | 2.6 | 12.0 | 15.2 |
| Median | 4.0 | 0.0 | 1.0 | 6.0 | 2.3 | 24.0 | 26.7 |

Some of the membrane-immobilized glomeruli were assessed for their suitability for immunopathology. FIG. 11 shows a picture of an indirect immunofluorescence pattern of a membrane-immobilized glomerulus reacted with fluorescein isothiocyanate (FITC)-conjugated coctail of anti-IgM and anti-IgA antibodies. FIG. 12 shows the same image as FIG. 11 filtered to reveal DNA with DAPI (4',6 diamino 2 phenylindole) counter stain. Glomeruli immobilized on BioDyne membrane were fixed in ice-cold 3% paraformaldehyde in Dulbecco's phosphate-buffered saline (D-PBS), washed in D-PBS, and incubated at 37° C. for 30 minutes using the recommended dilution of polyvalent fluorescein-congugated goat anti-human antibody (Dako-Pratt, Denmark). The membranes were then washed in D-PBS and mounted in 90% glycerol containing n-phenydiamine. Immunostained membranes were examined by epifluorescent microscopy using a Nikon Optiphot photomicroscope; photographs were recorded on Ilford PH-5 film.

Immunofluorescence of membrane-immobilized glomeruli was tested in nine cases, 5 showed no fluorescence, 4 were positive. The quality of the fluorescence was excellent, though the pattern of fluorescence was unusual in that these preparations had a three-dimensional character; thus, a case of IgA/membranous nephropathy appeared as a three-dimensional network of fluorescence rather than the typical linear pattern of fluorescence seen in sectioned tissue. With epifluorescent illumination the opacity of the nylon membrane substrate did not interfere the detection and examination of immune deposits, which appeared as fluorescent patches along the membrane surface (FIG. 11). Thus, membrane-immobilized glomeruli can be used for immunopathology. FIG. 13 shows an electron micrograph of a membrane-immobilized glomerulus.

The biopsy procedure, by its very nature, is an invasive and injurious technique designed to sample living tissues. While modern technology has helped reduce the morbid consequences of sampling, the current trend towards narrow-diameter biopsy needles also reduces the volume of tissue for pathological analysis and markedly increases the surface area to volume ratio of the biopsy core. For kidney biopsies this is of particular concern since glomeruli are apt to be dislodged from the surface of the core during handling and processing.

The actual number of glomeruli observed in clinical biopsy samples is substantially lower than the number predicted for a similar volume of normal kidney. While it is possible that this discrepancy may be explainable by changes in the numerical density of glomeruli in diseased kidneys, it seems improbable that such a large change (an order of magnitude) would occur in all the patients in our series, as these patients had diverse diagnoses and clinical histories. Without knowing the numerical density of glomeruli in various kidney diseases, it is difficult to reconcile the theoretical and practical data. However, based on the animal and clinical portions of this study, at least part of the difference between the actual and predicted numbers of glomeruli is due to the loss of glomeruli from the biopsy core once it is removed from the biopsy needle.

The results of the rabbit study suggest that while dislodged glomeruli are found at every stage of the biopsy procedure, the vast majority of glomeruli accumulate in the saline fluid, on the stainless steel dish, and on the microscope slide. Likewise, substantial numbers of dislodged human glomeruli accumulate in the saline and on the slide. Since a glomerulus is fundamentally a capillary tuft, it follows that cutting through its vascular pole would loosen its attachment to the biopsy core. Various mechanical and chemical dissociation methods have also been developed as research tools to isolate and collect glomeruli. Hence, we speculate that mechanical agitation may exacerbate the loosening of glomeruli from the core, particularly those whose vascular poles lie outside the biopsy cylinder. Moreover, exposing the biopsy cores, even briefly, to saline may further loosen the glomeruli from the core.

Not only are some glomeruli dislodged during processing, but a proportion of them can be retrieved and immobilized onto a membrane substrate. The immobilization of glomeruli onto membrane does not interfere with the routine clinical handling of biopsy core specimens. Immobilizing glomeruli on membranes, whether by filtration or by blotting, adds little additional time to the biopsy procedure. Most importantly, light and electron microscopy reveals that membrane-immobilized glomeruli can be used for routine pathological analysis. Thus, this simple and noninvasive approach offers a means for supplementing the quantity, and even quality of glomeruli, which may be of value in several situations. First, in cases where a biopsy core contain insufficient numbers of glomeruli, retrieved glomeruli could assist in making a diagnosis. Second, by increasing the total number of glomeruli, an opportunity exists to reduce the number of cores taken at biopsy. Third, retrieved glomeruli can provide additional tissue that can be archived for future analysis. (Epon-embedded membrane is easy to handle and archive). Thus, while the ultimate value of retrieving glomeruli depends on the individual case, the cost of retrieving lost glomeruli is relatively small. It is noteworthy that in all but one case, one or more glomerulus be retrieved for study. It should be noted that the value for "percent retrieved" includes the total number of glomeruli dislodged from any of the (two or three) biopsies manipulated in the saline or on the slide. It should also be noted that the number of retrieved glomeruli was determined by counting dark, osmium-stained glomeruli on Epon-embedded membranes, which were easily distinguished from other tissue fragments based on their characteristic morphological features. As the number of glomeruli visible after fixation was the same as the number visible after osmication suggests that once the glomeruli come in contact with the membrane that they are immobilized indefinitely. Surprisingly, the small size and intact isolation of membrane-immobilized glomeruli confer advantages over conventional core specimens. Their small size accelerated their fixation and processing for histopathology and ultrastructural pathology; their intact isolation made possible an overview of glomerular structure resembling a whole mount. These features might be of value in certain clinical settings and for research studies of glomerular structure and function. Indeed, preliminary experiments have shown that it is possible to maintain human membrane-immobilized glomeruli in tissue culture for up to 4 days with no significant deterioration in glomerular morphology as reported previously for tissue.

The present invention includes the discovery of the existence of a population of glomeruli that are normally lost during renal biopsy and method and apparatus for retrieving these lost glomeruli, which may have value in both clinical and basic science studies.

Accordingly, it is to be understood that the embodiments of the invention herein described are merely illustrative of the application of the principles of the invention. Reference herein to details of the illustrated embodiments are not intended to limit the scope of the claims, which themselves recite those features regarded as essential to the invention.

What is claimed is:

1. A method of retrieving glomeruli during a renal biopsy procedure that have been dislodged from a biopsy core taken during said renal biopsy procedure, wherein the method comprises:
   a) washing said core or instruments used to obtain said biopsy core in an appropriate solution for retrieval of a renal biopsy core:
   b) collecting said solution after it has been used to wash said biopsy core or said instruments; and
   c) filtering said collected solution through a porous membrane substrate such that any dislodged glomeruli are retrieved from said solution by immobilizing said dislodged glomeruli on said porous membrane substrate.

2. The method of claim 1 wherein said glomeruli on said porous membrane substrate are preserved by air drying, freeze drying or chemical fixation.

3. The method of claim 1 further comprising blotting instruments used to obtain or analyze said biopsy core that have been in contact with said biopsy core or said solution with a porous membrane after washing said instruments in said solution.

* * * * *